US012616491B2

(12) United States Patent　　　　(10) Patent No.: US 12,616,491 B2
Crawford et al.　　　　　　　　　　(45) Date of Patent:　May 5, 2026

(54) MEDICAL DEVICES AND RELATED METHODS THEREOF

(71) Applicant: Boston Scientific Scimed, Inc., Maple Grove, MN (US)

(72) Inventors: Richard Crawford, Galway (IE); Enda Connaughton, County Galway (IE); Paul E. Tierney, County Galway (IE); Peter Brady, Galway (IE); Molly Phillips-Hungerford, Somerville, MA (US); Naomi Gannon, Shrewsbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 272 days.

(21) Appl. No.: 18/404,085

(22) Filed: Jan. 4, 2024

(65) Prior Publication Data

US 2024/0225673 A1　　Jul. 11, 2024

Related U.S. Application Data

(60) Provisional application No. 63/479,411, filed on Jan. 11, 2023.

(51) Int. Cl.
*A61B 17/221*　　(2006.01)
*A61B 17/00*　　(2006.01)
*A61B 17/22*　　(2006.01)

(52) U.S. Cl.
CPC ...... *A61B 17/221* (2013.01); *A61B 17/00234* (2013.01); *A61B 2017/00323* (2013.01); *A61B 2017/00358* (2013.01); *A61B 2017/00526* (2013.01); *A61B 2017/22038* (2013.01); *A61B 2017/22051* (2013.01); *A61B 2017/2215* (2013.01)

(58) Field of Classification Search
CPC ............ A61B 17/221; A61B 17/22031; A61B 2017/00234; A61B 2017/00323; A61B 2017/00358; A61B 2017/00526; A61B 2017/22038; A61B 2017/22051; A61B 2017/2212; A61B 2017/2215; A61B 2017/2217; A61B 2017/22034; A61B 2017/22035; A61M 25/09; A61M 25/09041; A61M 2025/09116
USPC ......................................... 606/127
See application file for complete search history.

(56) References Cited

U.S. PATENT DOCUMENTS

| | | | |
|---|---|---|---|
| 6,692,484 B1 | 2/2004 | Karpiel et al. | |
| RE47,376 E | 5/2019 | Pokorney et al. | |
| 11,083,476 B2 | 8/2021 | Cheon et al. | |
| 2002/0072764 A1* | 6/2002 | Sepetka ............... | A61B 17/221 606/200 |
| 2005/0055047 A1* | 3/2005 | Greenhalgh ......... | A61B 17/221 606/200 |
| 2006/0129166 A1 | 6/2006 | Lavelle | |
| 2008/0188866 A1 | 8/2008 | Karpiel et al. | |
| 2021/0212708 A1 | 7/2021 | Bartholomai et al. | |

(Continued)

*Primary Examiner* — Kankindi Rwego
(74) *Attorney, Agent, or Firm* — Bookoff McAndrews PLLC

(57) ABSTRACT

A medical device including an actuator and a basket at a distal end of the actuator. The basket includes a plurality of wires and a plurality of eyelets extending from at least one wire of the plurality of wires, where the basket is configured to be transitioned from a collapsed configuration to an expanded configuration.

20 Claims, 4 Drawing Sheets

(56) References Cited

U.S. PATENT DOCUMENTS

| | | |
|---|---|---|
| 2021/0361306 A1 | 11/2021 | Guo et al. |
| 2022/0125448 A1 | 4/2022 | Xu et al. |
| 2022/0218416 A1 | 7/2022 | Vogel |

* cited by examiner

MEDICAL DEVICES AND RELATED METHODS THEREOF

CROSS-REFERENCE TO RELATED APPLICATIONS

This application claims the benefit of priority under 35 U.S.C. § 119 from U.S. Provisional Application No. 63/479,411, filed Jan. 11, 2023, which is incorporated by reference herein in its entirety.

TECHNICAL FIELD

Various aspects of this disclosure relate generally to medical treatment systems, devices, and related methods thereof. More specifically, embodiments of the disclosure relate to devices for treatment of, for example, blockages within the common bile duct and the pancreatic duct.

BACKGROUND

During a medical procedure, for example an endoscopic retrograde cholangiopancreatography, or ERCP, procedure, an operator may utilize endoscopic techniques to remove blockages, such as stones, or calculi, from the common bile duct. Occasionally, these blockages may be impacted into the wall of the bile duct, or may have a size which necessitates use of a wire basket to remove the blockages. However, a guidewire used to position a wire basket within the bile duct may not be ideally positioned with respect to the wire basket, making positioning of the basket and blockage retrieval difficult. Alternatively, the wire basket may not be positioned via a guidewire, which may result in accidental placement of the basket within the pancreatic duct. The current disclosure may solve one or more of these issues or other issues in the art.

SUMMARY

Each of the aspects disclosed herein may include one or more of the features described in connection with any of the other disclosed aspects.

Aspects of the disclosure relate to, among other things, systems, devices, and methods for removal of material from a lumen within the body of a patient (for example, within the common bile duct and/or the pancreatic duct) during medical procedures. Aspects of the disclosure also relate to, among other things, a retrieval basket having features, such as loops, for accommodating a guide wire and positioning the basket relative to the guide wire.

According to an example, a medical device may include an actuator and a basket at a distal end of the actuator. The basket may include a plurality of wires, and a plurality of eyelets extending from at least one wire of the plurality of wires, where the basket is configured to be transitioned from a collapsed configuration to an expanded configuration.

Any of the medical devices described herein may include any of the following features. The plurality of eyelets is formed integrally with the at least one wire of the plurality of wires. The plurality of eyelets includes at least 4 eyelets. In the expanded configuration, each of the wires of the plurality of wires is configured to be moved outwardly with respect to a central axis of the medical device. The plurality of eyelets extends from only one wire of the plurality of wires. A guide wire extending through each of the eyelets of the plurality of eyelets. In the expanded configuration, the guide wire is configured to be arranged at approximately a periphery of the basket. In the expanded configuration, the guide wire is configured to follow a shape of the at least one wire to which the plurality of eyelets is coupled. The guide wire is configured to extend through each of the eyelets of the plurality of eyelets from a proximal end of the basket to a distal end of the basket. Each of the eyelets includes a shape memory material. An aperture defined by each of the eyelets lies in a plane perpendicular to a central longitudinal axis of the basket. A diameter of each of the eyelets is in a range of 1 mm to 1.5 mm. In the collapsed configuration, the plurality of eyelets is configured to receive a shipping mandrel. One of the eyelets includes an atraumatic end cap disposed on a distalmost end of the basket. A sheath surrounding the actuator.

According to another example, a medical device may include an actuator, a basket at a distal end of the actuator, where the basket includes a plurality of wires, and a plurality of eyelets extending from at least one wire of the plurality of wires, where each of the plurality of eyelets is formed integrally with the at least one wire of the plurality of wires, and a guide wire extending through each of the eyelets of the plurality of eyelets, where the basket is configured to be transitioned from a collapsed configuration to an expanded configuration, and where in the expanded configuration, the guide wire is configured to follow a shape of the at least one wire having the plurality of eyelets.

Any of the medical devices disclosed herein may include any of the following features. The guide wire is configured to be arranged at approximately a periphery of the basket. Each of the eyelets includes a shape memory material.

According to another example, a method for manufacturing a medical device may include forming a plurality of loops in a first wire, where the first wire is in a first configuration, heating the first wire to a first temperature while the first wire is in the first configuration, joining the first wire to a plurality of wires to form a basket, transitioning the first wire to a second configuration, and heating the first wire to a second temperature while the first wire is in the second configuration.

Any of the methods disclosed herein may include any of the following features. Each wire of the plurality of wires does not include a loop.

It may be understood that both the foregoing general description and the following detailed description are exemplary and explanatory only and are not restrictive of the invention, as claimed. As used herein, the terms "comprises," "comprising," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "diameter" may refer to a width where an element is not circular. The term "top" refers to a direction or side of a device relative to its orientation during use, and the term "bottom" refers to a direction or side of a device relative to its orientation during use that is opposite of the "top." The term "distal" refers to a direction away from an operator/toward a treatment site, and the term "proximal" refers to a direction toward an operator. The term "exemplary" is used in the sense of "example," rather than "ideal." The term "approximately," or like terms (e.g., "substantially"), includes values+/−10% of a stated value.

BRIEF DESCRIPTION OF THE DRAWINGS

The accompanying drawings, which are incorporated in and constitute a part of this specification, illustrate aspects of this disclosure and together with the description, serve to explain the principles of the disclosure.

DETAILED DESCRIPTION

Embodiments of this disclosure relate to medical devices including at least one expandable structure configured to aid in the removal of material from a lumen within the body of a patient (for example, within the common bile duct and/or the pancreatic duct) during a medical procedure, for example during an endoscopic retrograde cholangiopancreatography (ERCP) procedure. During an ERCP procedure, a physician, or other operator, may utilize both endoscopic and fluoroscopic techniques to diagnose and treat issues arising in the common bile duct and in the pancreatic duct. In some instances, these issues may include the presence of material that block or partially block the lumen of the bile duct. That material can be, for example, stones, or calculi, which may need to be removed.

Figure 1:
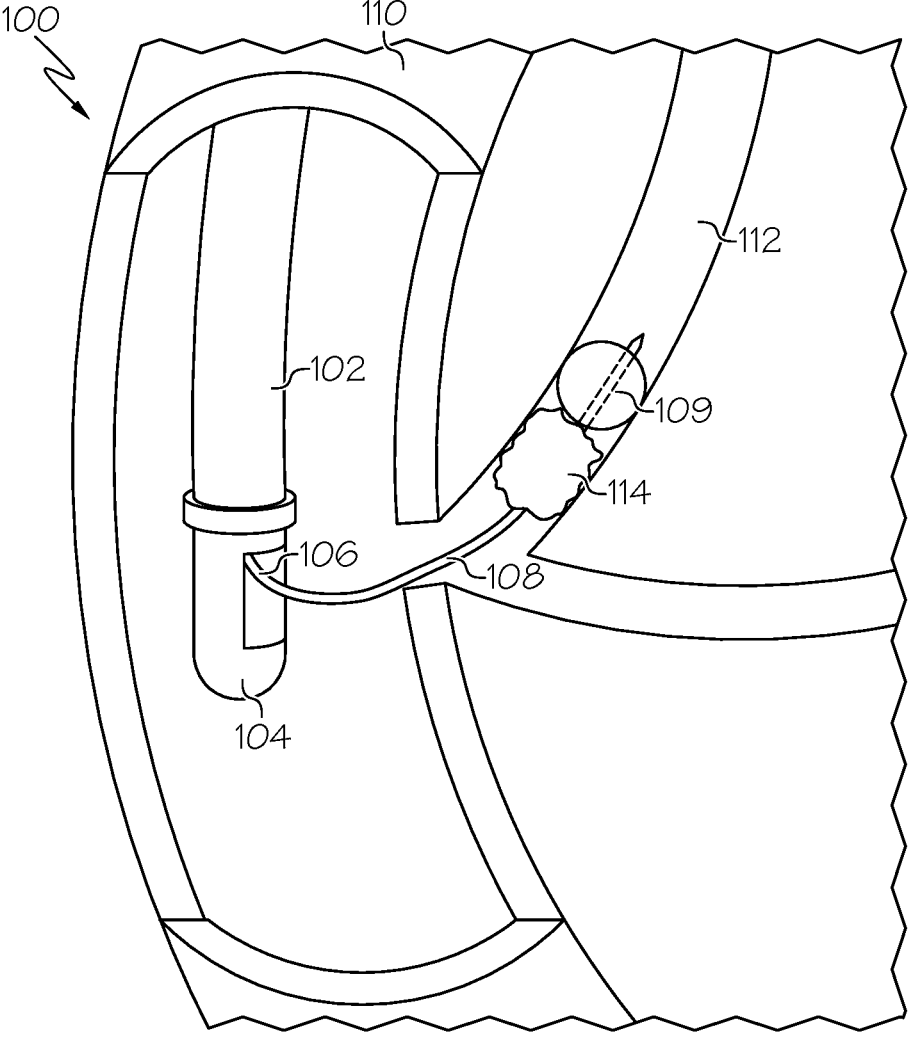
FIG. 1 shows an exemplary medical system during an endoscopic retrograde cholangiopancreatography (ERCP) procedure according to some embodiments.

For example, FIG. 1 depicts an exemplary medical system 100 during an ERCP procedure. Medical system 100 may include a duodenoscope 102 including an end cap 104 at a distal end of duodenoscope 102. Medical system 100 may additionally include an elevator 106 disposed within end cap 104, which may receive a retrieval device 108 through a working channel of duodenoscope 102. In some embodiments, retrieval device 108 may include at least one of a basket and/or a balloon 109 disposed at a distal end of retrieval device 108. During the procedure, duodenoscope 102 may be inserted into a duodenum 110 of a patient to remove material, for example gallstone 114, from a bile duct 112. Once end cap 104 is positioned adjacent to the opening to bile duct 112, elevator 106 may be actuated to direct retrieval device 108 toward the opening to bile duct 112. For example, in some embodiments, elevator 106 may be moved either upward or downward with respect to end cap 104 to direct retrieval device 108 towards the opening.

Once elevator 106 is in a desired position, retrieval device 108 may be deployed into bile duct 112 by translating device 108 distally. In some instances, retrieval device 108 may be deployed into bile duct 112 such that a distalmost end of retrieval device 108 extends past gallstone 114 within bile duct 112. Subsequently, balloon 109 may be inflated, in at least some instances expanding the walls of bile duct 112. Once inflated, the physician, or other operator using medical system 100, may begin to pull retrieval device 108 out of bile duct 112. If gallstone 114 is small enough, the pressure of balloon 109 against gallstone 114 may be adequate to dislodge gallstone 114 from bile duct 112 and push it out of bile duct 112 into duodenum 110. However, in some instances, gallstone 114 may be too large for removal via balloon 109, or may be impacted into a wall of bile duct 112 such that a different removal technique may be necessary.

Accordingly, in some embodiments, a retrieval device may include a wire basket at a distal end of the retrieval device. The basket may be configured to expand from a first, collapsed, configuration, to a second, expanded, configuration. Similar to balloon 109, when the basket is in the collapsed configuration, it may be extended into the bile duct until it is adjacent to, including past, gallstone 114. Subsequently, the basket may be expanded into the expanded configuration such that the basket surrounds gallstone 114. Once gallstone 114 is surrounded, the basket may be at least partially returned to the collapsed configuration such that gallstone 114 may be secured within the basket. The basket may then be further collapsed to help crush gallstone 114 before being removed from bile duct 112 by moving retrieval device 108 proximally with respect to duodenoscope 102.

While some wire baskets typically used in ERCP procedures are effective in removing material, such as calculi, there may be some limitations. For example, many wire baskets may not be coupled, or sufficiently coupled, to a guide wire during insertion and positioning if the basket within the bile duct. This can make proper insertion and positioning challenging, and could result in the basket being inserted into the pancreatic duct, which could harm the patient. Alternatively, a wire basket may be coupled to a guide wire, but the guide wire axis may be positioned at an angle (transverse to) the long axis of the basket, which may create challenges while positioning the basket. In some cases, a guide wire may extend centrally through the basket, which may impede the ability to capture the calculus centrally within the basket. Accordingly, there is a need for a wire-guided basket capable of being easily and accurately positioned within the bile duct, without having a compromised capability to capture calculi.

Figure 2:
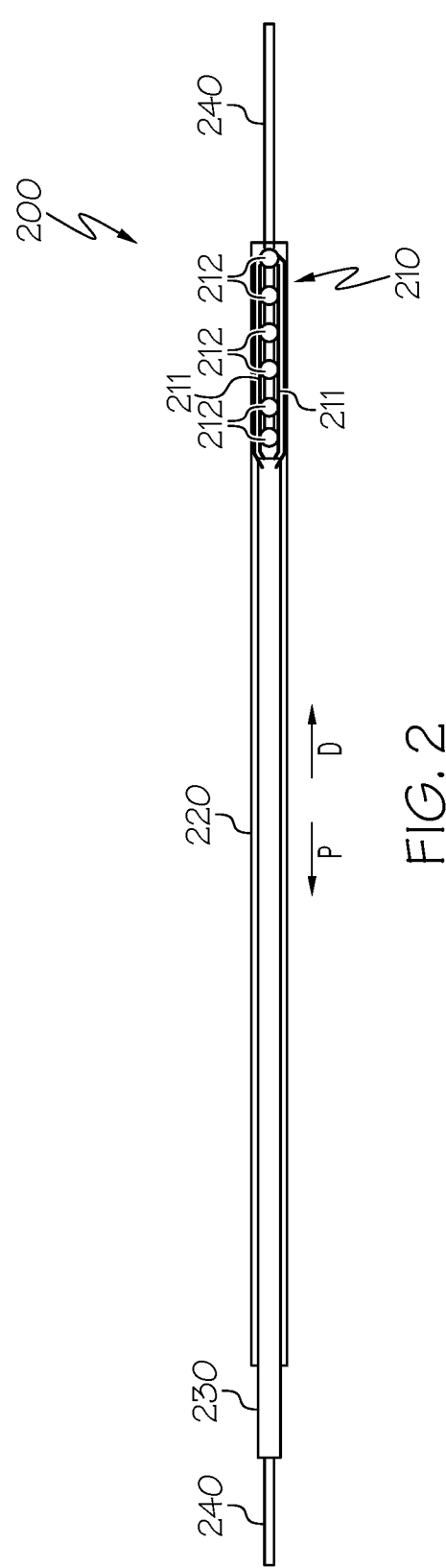
FIG. 2 shows a side view of an exemplary medical device in a collapsed configuration according to some embodiments.
Figures 3A, 3B:
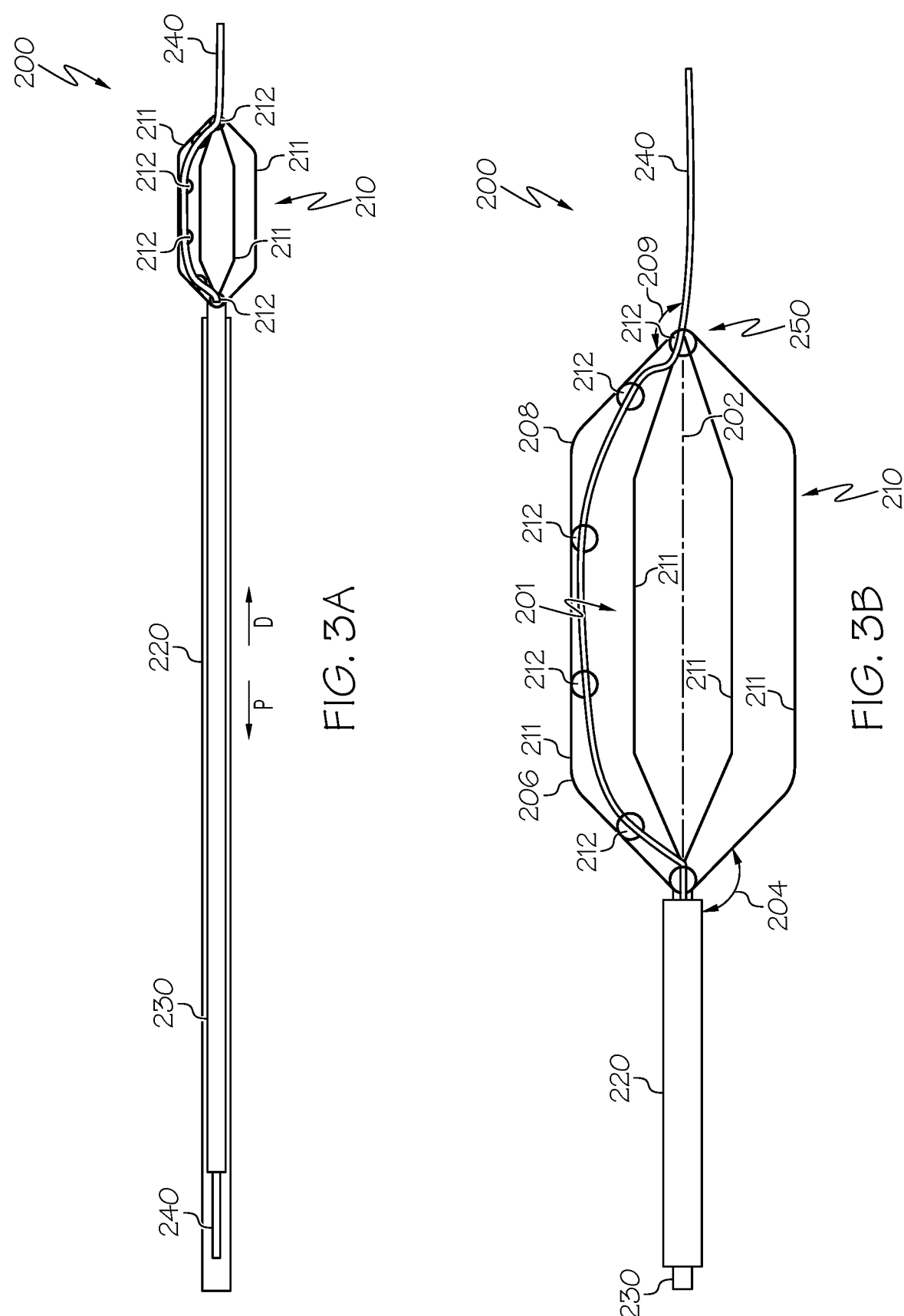
FIG. 3A shows a side view of an exemplary medical device in an expanded configuration according to some embodiments.
FIG. 3B shows a zoomed-in view of a basket portion of the exemplary medical device of FIG. 3A according to some embodiments.

FIG. 2 shows a side view of an exemplary medical device, including a wire basket, in a collapsed configuration according to some embodiments. In FIG. 2, a medical device 200 having a wire basket is shown extending on a guide wire 240, from a proximal end of medical device 200 to a distal end of medical device 200. As shown in both FIGS. 2 and 3A, a proximal direction is indicated by the arrow "P," and a distal direction of FIGS. 2 and 3A is indicated by the arrow "D." Guide wire 240 may extend through an actuator 230, which may extend through a sheath 220. However, in some embodiments, guide wire 240 may be inserted into actuator 230 at a point in between a proximal end of actuator 230 and a distal end of actuator 230. For example, guide wire 240 may be inserted into actuator 230 at a point approximately 30 cm from a distal end of actuator 230.

In some embodiments, a basket 210 may couple to actuator 230 at a distal end of actuator 230. Basket 210 may be configured to be transitioned from a collapsed configuration, as shown in FIG. 2, for example, to an expanded configuration, as shown in FIGS. 3A and 3B.

Still referring to FIG. 2, basket 210 may include a plurality of wires 211, extending from a proximal end of basket 210 to a distal end of basket 210. In some embodiments, basket 210 may include at least 3 wires; however, basket 210 may include any number of wires (e.g., 4, 6, 8, etc.) suitable to allow for adequate spacing between adjacent wires, such that a calculus may fit between the wires when basket 210 is in an expanded position. Wires 211 may be made of stainless steel, nitinol, other metal alloys, plastic, or any other material suitable for use in medical devices, and capable of being transitioned from a first position to a second position.

In some embodiments, basket 210 may include features configured to receive a guidewire. Basket 210, for example, includes a plurality of eyelets 212 coupled to, or integral with, at least one of wires 211. Eyelets 212 may be spaced apart from each other along a length of wire 211, and may be configured to receive guide wire 240 therethrough. Spacing between eyelets 212 may be uniform or variable. Guide wire 240 may extend through each of eyelets 212 from a proximal end of basket 210 to a distal end of basket 210. Accordingly, because eyelets 212 are coupled to, or integral with, one of wires 211, guide wire 240 may also be moveably coupled to one of wires 211 in a fashion that prevents guide wire 240 from extending directly through the middle of basket 210. Guide wire 240 instead extends along wire 211 having eyelets 212.

In some embodiments, eyelets 212 may be made from a shape memory material, such as nitinol, or any other material that wire 211 is made from. Each eyelet 212 defines an aperture therethrough having a width or a diameter large enough to receive guide wire 240. In some embodiments, eyelets 212 may define an aperture having a width or diameter in a range of about 1 mm to about 1.5 mm. However, in some embodiments, a width or a diameter of the apertures of eyelets 212 may be scaled up or down depending on a size of basket 210, guide wire 240, and/or the procedure to be performed.

Figure 4:
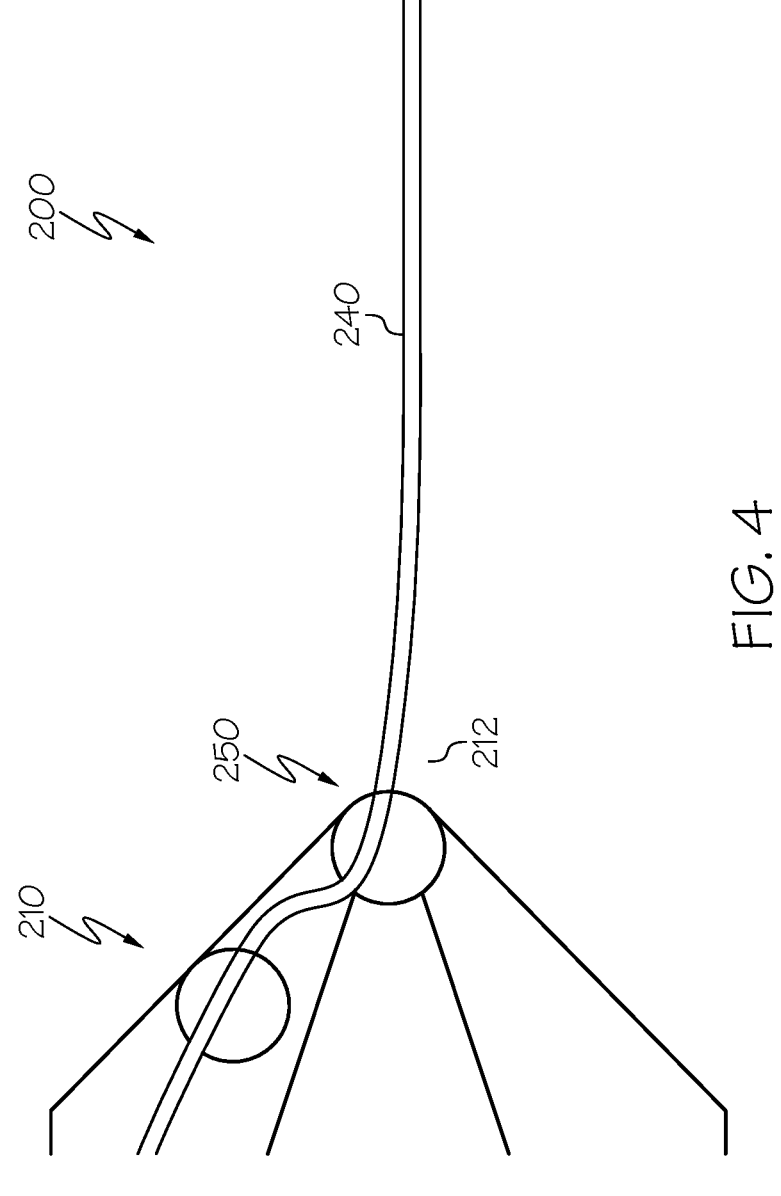
FIG. 4 shows a side view of a distal end of a basket portion of an exemplary medical device according to some embodiments.

FIGS. 2-4 show side views of medical device 200. Eyelets 212, however, are shown in a perspective view to show apertures defined by eyelets 212 and guide wire 240 extending through those apertures. It is understood that a plane that an eyelet 212, and its defined aperture, lie in is perpendicular or approximately perpendicular to axis 202. The apertures of eyelets 212 face distally. In some embodiments, the planes of eyelets 212 may be at other angles to axis 202.

FIGS. 3A and 3B illustrate side views of an exemplary medical device, including a wire basket, in an expanded configuration according to some embodiments. When in the expanded position, each of wires 211 may be moved from the collapsed position, shown in FIG. 2, outwardly with respect to a central axis 202 of medical device 200, and may form a compartment 201 therebetween, which may be configured to receive a calculus. In the expanded position, each of wires 211 may extend distally from actuator 230 at a first angle 204 with respect to central axis 202. At a first point 206, wires 211 may be bent such that wires 211 extend parallel or substantially parallel to central axis 202 until they reach a second point 208 at which there is another bend. At second point 208, wires 211 may extend distally toward an end cap 250 at a second angle 209 with respect to central axis 202. In alternative embodiments, instead of having sharp bends, each wire 211 may have a gentle curvature from a proximal end of basket 210 to end cap 250. End cap 250 may be one of the eyelets 212 (the most distal eyelet 212) formed from wire 211.

As shown in FIGS. 3A and 3B, when basket 210 is in the expanded position, guide wire 240 may follow the shape of the wire 211 to which it is coupled. Accordingly, during an ERCP procedure, guide wire 240 may remain on the periphery of basket 210, thereby allowing a calculus to enter basket 210 without being impeded. Furthermore, the positioning of guide wire 240 along the periphery of basket 210 may aid in accurately positioning basket 210 within bile duct 112, as the guide wire axis (distal to the basket 210) is positioned along, and not transverse to, axis 202 of basket 210.

FIG. 4 shows a side view of a distal end of a basket portion of an exemplary medical device according to some embodiments. As shown, in some embodiments, basket 210 may include an end cap, for example atraumatic end cap 250 disposed at a distalmost end of basket 210. Atraumatic end cap 250 may be a distalmost eyelet of wire 211, and may be the distalmost end of that wire 211. End cap 250 may be configured to help mitigate potential damage to tissue that could be caused by the distal end of basket 210 if it were left without an end cap 250 or otherwise uncovered. All of wires 211 meet at end cap 250. Each wire 211 may join end cap 250 along the outer periphery of end cap 250/distalmost eyelet 212.

As mentioned above, in some embodiments, eyelets 212 may be formed from a shape memory material such as nitinol. Accordingly, eyelets 212 may be formed by creating a plurality of loops in at least one of wires 211, which may then be heated to a suitable temperature known in the art to effectively "store" the shape of the loops. In some embodiments, the eyelets may be set while the wire 211 is in a straight configuration, before that wire 211 is bent or otherwise shaped, and joined with other wires, to form basket 210. Wire 211 having eyelets 212 may be re-set when the wire 211 is in the expanded configuration to help ensure accurate alignment and placement of guide wire 240 while basket 210 is in the expanded configuration.

In some embodiments, a shipping mandrel may be inserted through eyelets 212 when basket 210 is in the collapsed position. The shipping mandrel may help maintain the shape of eyelets 212 while medical device 200 is being packaged, shipped, and stored prior to use. The shipping mandrel may be removed from eyelets 212 and replaced with guide wire 240 while medical device 200 is being prepared for use in a medical procedure.

During a medical procedure, for example an ERCP procedure, a physician or other operator may utilize medical device 200 to aid in the removal of a calculus, for example a gallstone, from a bile duct of a patient. For example, medical device 200 may be used in the procedure described above with respect to FIG. 1. In a procedure using medical device 200, however, device 200 is navigated to the desired position by translating device 200 over an already-placed guide wire 240, while guide wire 240 is within eyelets 212. After proper positioning of device 200, guide wire 240 may be removed from at least basket 210, basket 210 may be deployed from the collapsed position to the expanded position and then used to capture a gallstone or other material within the duct. Once the gallstone is captured within basket 210, basket 210 may be transitioned back to the collapsed configuration to help crush the gallstone before basket 210 is removed from the bile duct.

While principles of this disclosure are described herein with reference to illustrative examples for particular applications, it should be understood that the disclosure is not limited thereto. For example, the disclosure refers to ERCP as an exemplary procedure, and the bile and pancreatic ducts as typical lumens for the systems and methods of the disclosure. The systems, devices, and methods of the present disclosure, however, may be used in any suitable medical procedure in any lumen or cavity within the body, for example, to remove any unwanted material from the body. Those having ordinary skill in the art and access to the teachings provided herein will recognize additional modifications, applications, and substitution of equivalents all fall within the scope of the examples described herein. Accordingly, the invention is not to be considered as limited by the foregoing description.

What is claimed is:

1. A medical device, comprising:

an actuator; and a basket at a distal end of the actuator, wherein the basket comprises:

a plurality of wires, and a plurality of eyelets extending from at least one wire of the plurality of wires, wherein the basket is configured to be transitioned from a collapsed configuration to an expanded configuration, wherein, in the expanded configuration, each of the wires of the plurality of wires is configured to be moved outwardly with respect to a central axis of the medical device.

2. The medical device of claim 1, wherein the plurality of eyelets is formed integrally with the at least one wire of the plurality of wires.

3. The medical device of claim 1, wherein the plurality of eyelets includes at least 4 eyelets.

4. The medical device of claim 1, wherein the plurality of eyelets extends from only one wire of the plurality of wires.

5. The medical device of claim 1, further comprising a guide wire extending through each of the eyelets of the plurality of eyelets.

6. The medical device of claim 5, wherein in the expanded configuration, the guide wire is configured to be arranged at approximately a periphery of the basket.

7. The medical device of claim 5, wherein in the expanded configuration, the guide wire is configured to follow a shape of the at least one wire to which the plurality of eyelets is coupled.

8. The medical device of claim 5, wherein the guide wire is configured to extend through each of the eyelets of the plurality of eyelets from a proximal end of the basket to a distal end of the basket.

9. The medical device of claim 1, wherein each of the eyelets includes a shape memory material.

10. The medical device of claim 1, wherein an aperture defined by each of the eyelets lies in a plane perpendicular to a central longitudinal axis of the basket.

11. The medical device of claim 1, wherein a diameter of each of the eyelets is in a range of 1 mm to 1.5 mm.

12. The medical device of claim 1, wherein in the collapsed configuration, the plurality of eyelets is configured to receive a shipping mandrel.

13. The medical device of claim 1, further comprising a sheath surrounding the actuator.

14. The medical device of claim 1, wherein one of the eyelets comprises an atraumatic end cap disposed on a distalmost end of the basket.

15. A medical device, comprising:

an actuator; and a basket at a distal end of the actuator, wherein the basket comprises:

a plurality of wires, and a plurality of eyelets extending from at least one wire of the plurality of wires, wherein the basket is configured to be transitioned from a collapsed configuration to an expanded configuration, wherein one of the eyelets comprises an atraumatic end cap disposed on a distalmost end of the basket.

16. The medical device of claim 15, further comprising a guide wire extending through each of the eyelets of the plurality of eyelets, wherein in the expanded configuration, the guide wire is configured to be arranged at approximately a periphery of the basket.

17. The medical device of claim 15, wherein the plurality of eyelets includes at least 4 eyelets.

18. A medical device, comprising:

an actuator;

a basket at a distal end of the actuator, wherein the basket comprises:

a plurality of wires, and a plurality of eyelets including at least 4 eyelets, the plurality of eyelets extending from at least one wire of the plurality of wires, wherein the basket is configured to be transitioned from a collapsed configuration to an expanded configuration.

19. The medical device of claim 18, further comprising a guide wire extending through each of the eyelets of the plurality of eyelets, wherein the guide wire is configured to be arranged at approximately a periphery of the basket.

20. The medical device of claim 18, wherein each of the eyelets includes a shape memory material.

* * * * *